United States Patent
Tajima et al.

(10) Patent No.: US 8,273,843 B2
(45) Date of Patent: Sep. 25, 2012

(54) ORGANOSILICON COMPOUND AND THERMOSETTING RESIN COMPOSITION CONTAINING THE SAME

(75) Inventors: Akio Tajima, Ichihara (JP); Kazuhiro Yoshida, Ichihara (JP)

(73) Assignee: JNC Corporation, Tokyo (JP)

( * ) Notice: Subject to any disclaimer, the term of this patent is extended or adjusted under 35 U.S.C. 154(b) by 175 days.

(21) Appl. No.: 12/765,215

(22) Filed: Apr. 22, 2010

(65) Prior Publication Data

US 2010/0273937 A1 Oct. 28, 2010

(30) Foreign Application Priority Data

Apr. 24, 2009 (JP) .................. 2009-106751

(51) Int. Cl.
*C08G 77/12* (2006.01)

(52) U.S. Cl. ................ 528/31; 528/32; 528/27

(58) Field of Classification Search .............. 528/31, 528/32, 27
See application file for complete search history.

(56) References Cited

U.S. PATENT DOCUMENTS 6,313,255 B1 * 11/2001 Rubinsztajn .................. 528/27

FOREIGN PATENT DOCUMENTS

| JP | 61-112334 | 5/1986 |
|---|---|---|
| JP | 2-289611 | 11/1990 |
| JP | 2003-277473 | 10/2003 |
| JP | 2004-27186 | 1/2004 |
| JP | 2004-331647 | 11/2004 |
| JP | 2006-070049 | 3/2006 |
| WO | 03-024870 | 3/2003 |
| WO | 2004-024741 | 3/2004 |
| WO | 2004-081084 | 9/2004 |

* cited by examiner

*Primary Examiner* — Kuo-Liang Peng
(74) *Attorney, Agent, or Firm* — J.C. Patents

(57) ABSTRACT

An organosilicon compound which is obtained by subjecting a compound (A), a compound (B) and a compound (C) to hydrosilylation reaction: (A) silicone and/or silsesquioxane that has two or more Si—H groups per one molecule and has a molecular weight of 100 to 500,000; (B) silicone and/or silsesquioxane that has two or more alkenyl groups per one molecule and has a molecular weight of 100 to 500,000; and (C) a compound that has one or more epoxy or oxetanyl group and an alkenyl group having 2 to 18 carbon atoms per one molecule.

13 Claims, No Drawings

ORGANOSILICON COMPOUND AND THERMOSETTING RESIN COMPOSITION CONTAINING THE SAME

BACKGROUND OF THE INVENTION

1. Field of the Invention

The present invention relates to a novel organosilicon compound, a thermosetting resin composition containing the compound useful for such purposes as a coating material, an optical material and an electric insulating material, and a cured material which is obtained by thermally heat-curing the composition.

2. Related Art

In recent years, an illumination device, such as a light emitting diode (LED), which is subjected to practical use as a display board, a light source for an image scanner, a traffic signal, a large-sized display unit, a backlight for a mobile phone, and the like, is generally produced by sealing with a resin system, which contains an aromatic epoxy resin having an alicyclic acid anhydride added thereto as a curing agent. However, it has been known that the resin system is liable to suffer discoloration of the acid anhydride due to an acid, and requires a prolonged period of time for curing. Furthermore, the resin system has a problem of yellowing of the sealing resin when the sealing resin is exposed outdoors or exposed to a light source emitting an ultraviolet ray.

For solving the problems, it has been proposed that an LED or the like is sealed with an alicyclic epoxy resin or an acrylic resin cured with a cationic polymerization initiator (see, for example, JP-A-61-112334 and JP-A-2-289611). However, the cured resin having been cationically polymerized has such severe defects that the cured resin is extremely brittle and thus is liable to suffer breakage due to cracking through a cold cycle, and suffers significant discoloration of the sealing resin after curing as compared to the conventional curable resin system containing an aromatic epoxy resin and an acid anhydride. Accordingly, the curable resin system employing cationic polymerization is not suitable for a purpose that requires colorless transparency, particular not suitable for a purpose of sealing an LED, which requires heat resistance and transparency.

JP-A-2003-277473 discloses a resin composition for an LED sealing material that is prevented from suffering cracks through a cold cycle and is excellent in light fastness. The resin composition contains a hydrogenated epoxy resin or an alicyclic epoxy resin as a matrix component, but the resin composition suffers significant discoloration after curing and thus still has room for improvement in discoloration.

JP-A-2004-27186 discloses a potting resin composition containing an alicyclic epoxy resin or an oxetane resin as a viscosity decreasing agent for filling a gap between a circuit board and an electronic part disposed thereon. However, the resin composition contains a large amount of an inorganic filler and thus cannot be applied to a purpose that requires transparency. WO 01/072857 discloses an alkali aqueous solution-soluble resin composition containing a modified oxetane resin as an active energy ray-curable resin, but what is disclosed in this reference is to intend to provide an alkali-soluble resin, and a modified oxetane resin and a polyfunctional oxetane resin unavoidably suffer discoloration through thermal history due to an unsaturated bond contained therein.

JP-A-2006-070049, WO 2004/081084, JP-A-2004-331647, WO 2003/24870 and WO 2004/24741 each disclose a cage silicon compound and a polymer thereof, but fail to disclose the organosilicon compound and the thermosetting resin composition containing the same according to the invention.

SUMMARY OF THE INVENTION

An object of the invention is to provide a thermosetting resin composition that is capable of providing a cured material excellent in heat resistance and transparency. Another object of the invention is to provide a cured material and a molded article containing the thermosetting resin composition.

As a result of earnest investigations made by the inventors for achieving the aforementioned and other objects, the inventors have successfully synthesized a novel organosilicon compound, and have found that a thermosetting resin composition containing the compound and a curing agent is excellent in transparency, heat resistance, heat yellowing resistance and the like, thereby completing the invention.

The invention relates to the following aspects.

(1) An organosilicon compound which is obtained by subjecting a compound (A), a compound (B) and a compound (C) to hydrosilylation reaction:

(A) silicone and/or silsesquioxane that has two or more Si—H groups per one molecule and has a molecular weight of 100 to 500,000;

(B) silicone and/or silsesquioxane that has two or more alkenyl groups per one molecule and has a molecular weight of 100 to 500,000; and (C) a compound that has one or more epoxy or oxetanyl group and has an alkenyl group having 2 to 18 carbon atoms per one molecule.

(2) The organosilicon compound according to the item (1), wherein the compound (A) is at least one compound selected from the group consisting of compounds represented by the formulae (a-1) to (a-7);

the compound (B) is at least one compound selected from the group consisting of compounds represented by the formulae (b-1) and (b-2); and the compound (C) is at least one compound selected from the group consisting of compounds represented by the formulae (c-1), (c-2) and (c-3):

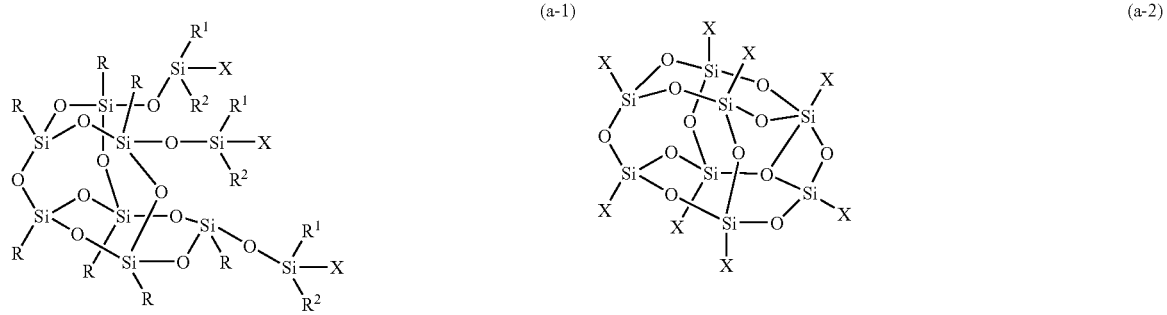

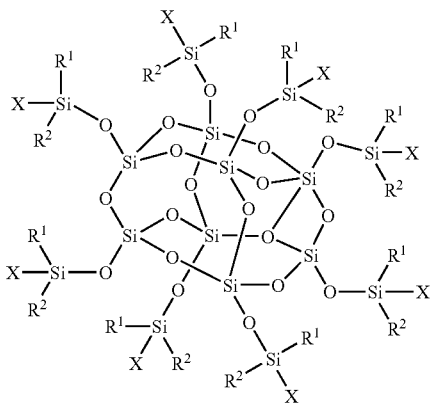
(a-3)

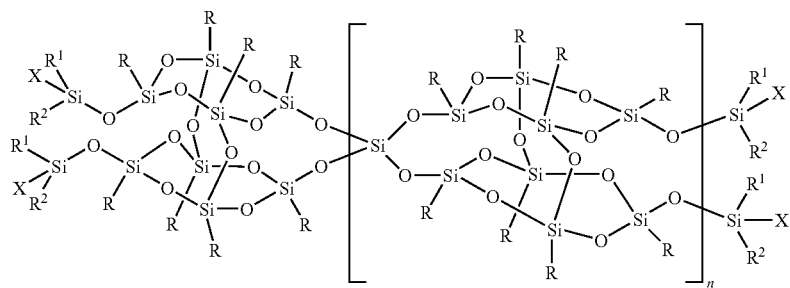
(a-4)

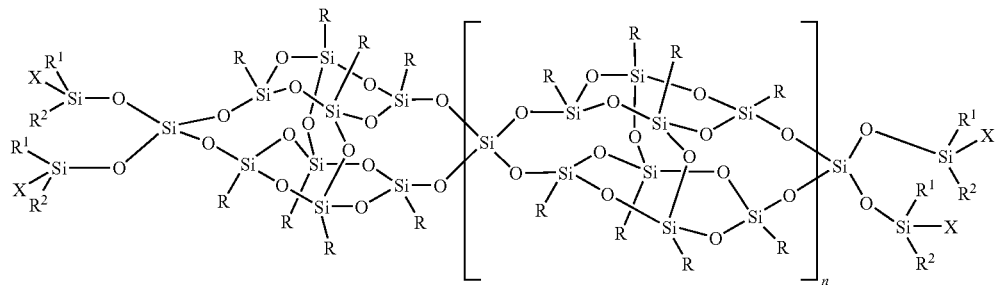
(a-5)

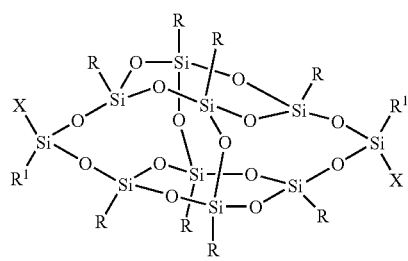
(a-6)

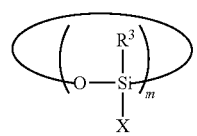
(a-7)

wherein in the formulae (a-1) to (a-7),

R represents a group selected independently from alkyl having 1 to 45 carbon atoms, cycloalkyl having 4 to 8 carbon atoms, aryl having 6 to 14 carbon atoms and arylalkyl having 7 to 24 carbon atoms, wherein in the alkyl having 1 to 45 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced; in the benzene ring in the aryl and the arylalkyl, arbitrary hydrogen may be replaced by halogen or alkyl having 1 to 10 carbon atoms, and in the alkyl having from 1 to 10 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced; and the alkylene in the arylalkyl has 1 to 10 carbon atoms, in which in the alkylene, arbitrary —$CH_2$— may be replaced by —O—, provided that two —$CH_2$— adjacent to each other are not simultaneously replaced, $R^1$ and $R^2$ each represent a group selected independently from alkyl having 1 to 4 carbon atoms, cyclopentyl, cyclohexyl and phenyl, $R^3$ represents a group selected independently from alkyl having 1 to 4 carbon atoms, cyclopentyl, cyclohexyl and phenyl, at least two of X each represent hydrogen, and the remainder of X represents a group selected independently from alkyl having 1 to 4 carbon atoms, cyclopentyl, cyclohexyl and phenyl, n represents an integer of 0 to 100, and m represents an integer of 3 to 10,

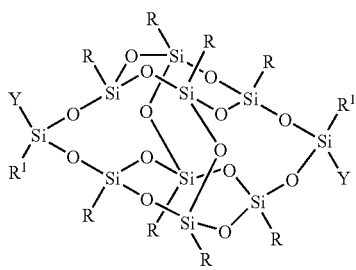
(b-1)

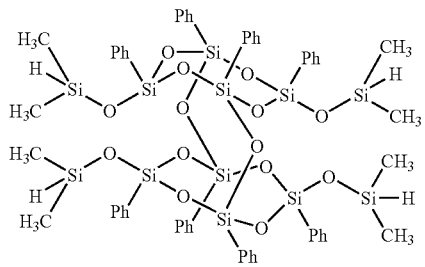
(a-4-1)

(4) The organosilicon compound according to the item (2) or (3), wherein the compound (B) is represented by the formula (b-1-1) or (b-2-1):

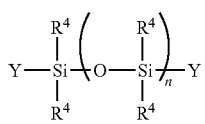
(b-2)

wherein in the formulae (b-1) and (b-2),

R and $R^1$ have the same meaning as R and $R^1$ for the formulae (a-1) to (a-6), respectively, $R^4$ represents a group selected independently from alkyl, cyclopentyl, cyclohexyl and phenyl, Y represents a group selected independently from vinyl and allyl, and n represents an integer of 0 to 100,

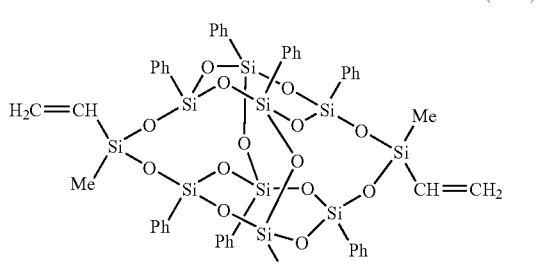
(b-1-1)

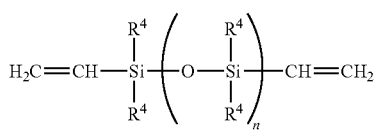
(b-2-1)

wherein $R^4$ represents a group selected independently from methyl and phenyl, and n represents an integer of 0 to 100.

(5) The organosilicon compound according to one of the items (2) to (4), wherein the compound (C) is at least one compound selected from the group consisting of compounds represented by the formulae (c-1-1), (c-2-1), (c-3-1) and (c-3-2):

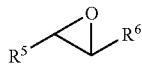
(c-1)

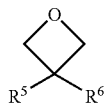
(c-2)

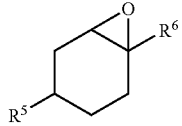
(c-3)

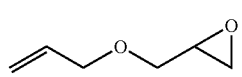
(c-1-1)

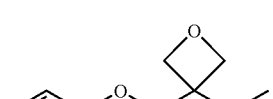
(c-2-1)

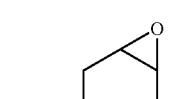
(c-3-1)

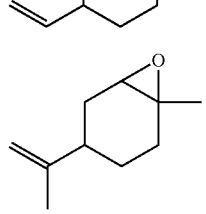
(c-3-2)

wherein in the formulae (c-1), (c-2) and (c-3), one of $R^5$ and $R^6$ represents alkenyl having 2 to 10 carbon atoms in which one —$CH_2$— may be replaced by —O— or 1,4-phenylene, and the other of $R^5$ and $R^6$ represents hydrogen or alkyl having 1 to 6 carbon atoms.

(3) The organosilicon compound according to the item (2), wherein the compound (A) is a silsesquioxane derivative represented by the formula (a-4-1):

(6) A thermosetting resin composition containing the organosilicon compound according to one of the items (1) to (5), and a curing agent.

(7) The thermosetting resin composition according to the item (6), wherein the curing agent is an acid anhydride.

(8) The thermosetting resin composition according to the item (6) or (7), wherein the thermosetting resin composition further contains a diluent, a curing accelerator and an additive.

(9) The thermosetting resin composition according to the item (8), wherein the diluent is an epoxy resin containing no silicon atom in a molecule thereof, an oxetane resin containing no silicon atom in a molecule thereof, or an organic solvent.

(10) The thermosetting resin composition according to the item (8), wherein the additive is an ultraviolet ray absorbent and/or an antioxidant.

(11) A cured material which is obtained by heat-curing the thermosetting resin composition according to one of the items (6) to (10).

(12) A molded article which is obtained by molding the cured material according to the item (11).

(13) A coated film which is obtained by coating a film with the thermosetting resin composition according to one of the items (6) to (10).

A cured material of the thermosetting resin composition of the invention is excellent, for example, in transparency, heat resistance, heat yellowing resistance and the like. Therefore, a molded article formed of the cured material can, be used favorably as a sealant for a semiconductor, a sealant for an optical semiconductor, an insulating film, a sealing material, an optical lens and the like. The resin composition can also be used as a transparent material, an optical material, an optical film, an optical sheet, an adhesive, an electronic material, an insulating material, an interlayer dielectric film, a coating composition, an ink, a coating material, a molding material, a potting material, a liquid crystal sealing material, a sealing material for a display device, a sealing material for a solar cell, a resist material, a color filter, an electronic paper material, a hologram material, a solar cell material, a fuel cell material, a display material, a recording material, a waterproofing material, a moisture proofing material, a solid electrolyte for a battery, a gas separation film and the like. The resin composition can also be used as an additive or the like for other resins.

DESCRIPTION OF PREFERRED EMBODIMENTS

The terms used herein will be described.

A compound represented by the formula (1) may be expressed as a compound (1) in some cases. Compounds represented by the other formulae may be expressed in the similar abbreviation manner. The term "arbitrary" used for describing the structures of the compounds includes not only an arbitrary position but also an arbitrary number. For example, the expression "arbitrary A may be replaced by B or C" not only includes the case where at least one of A is replaced by B, and the case where at least one of A is replaced by C, but also includes the case where at least one of A is replaced by B, and simultaneously another at least one of A is replaced by C. In the definition in alkyl or alkylene that arbitrary —$CH_2$— may be replaced by —O— does not include the case where plural —$CH_2$— adjacent to each other are all replaced by —O—. In the examples, the weights are data based on values expressed by a mass unit "g" (gram) displayed on an electronic balance. The percents by weight and the weight ratios are based on the values.

Organosilicon Compound

The organosilicon compound of the invention is obtained by subjecting the compound (A), the compound (B) and the compound (C) to hydrosilylation reaction.

The compound (A) is silicone and/or silsesquioxane that has two or more Si—H groups per one molecule and has a molecular weight of 100 to 500,000, and preferably 1,000 to 100,000.

The compound (B) is silicone and/or silsesquioxane that has two or more alkenyl groups per one molecule and has a molecular weight of 100 to 500,000, and preferably 150 to 10,000.

The compound (C) is a compound that has one or more epoxy group or oxetanyl group per one molecule and has an alkenyl group having 2 to 18 carbon atoms.

In the organosilicon compound of the invention, the ratio of the constitutional units derived from the compound (A), the compound (B) and the compound (C), respectively, is shown by the following expression:

$$(a \times \alpha) \geq (b \times \beta) + (c \times \gamma)$$

wherein a represents the molar fraction of the compound (A), b represents the molar fraction of the compound (B), c represents the molar fraction of the compound (C), α represents the number of Si—H groups contained in one molecule of the compound (A), β represents the number of alkenyl groups contained in one molecule of the compound (B), and γ represents the number of alkenyl groups contained in one molecule of the compound (C).

The hydrosilylation reaction of the compound (A), the compound (B) and the compound (C) may be carried out by adding the compound (A), the compound (B) and the compound (C) simultaneously, and is preferably carried out in such a manner that the compound (A) and the compound (B) are subjected to hydrosilylation reaction where (molar number of Si—H groups contained in (A))>(molar number of alkenyl groups in (B)), and then an excessive amount of the compound (C) is added thereto to perform hydrosilylation reaction of the unreacted Si—H groups and the alkenyl groups of the compound (C).

The hydrosilylation reaction is preferably carried out in a solvent.

The solvent used in the hydrosilylation reaction is not particularly limited as far as progress of the reaction is not inhibited thereby, and preferred examples of the solvent include a hydrocarbon solvent, such as hexane and heptane, an aromatic hydrocarbon solvent, such as benzene, toluene and xylene, an ether solvent, such as diethyl ether, tetrahydrofuran (THF) and dioxane, a halogenated hydrocarbon solvent, such as methylene chloride and carbon tetrachloride, and an ester solvent, such as ethyl acetate. The solvents may be used solely or as a combination of two or more kinds thereof. Among the solvents, an aromatic hydrocarbon solvent is preferred, and toluene is particularly preferred.

The hydrosilylation reaction may be carried out at room temperature or under heating for accelerating polymerization, and may be carried out under cooling for controlling heat generation through the polymerization, unfavorable polymerization and the like. A catalyst may be used in the polymerization through hydrosylilation reaction. The use of a hydrosilylation catalyst makes the polymerization proceed easily. Preferred examples of the hydrosilylation catalyst include a Karstedt catalyst, a Spier catalyst and hexachloroplatinic acid, which are ordinarily known catalysts. Only a small amount of the hydrosilylation catalysts used sufficiently makes the reaction proceed owing to high reactivity thereof. The amount of the catalyst used is generally $10^{-9}$ to 1% by mol, and preferably $10^{-7}$ to $10^{-3}$% by mol, in terms of the ratio of the transition metal contained in the catalyst with respect to the hydrosilyl groups.
Examples of the compound (A) include compounds represented by the following formulae (a-1) to (a-7).
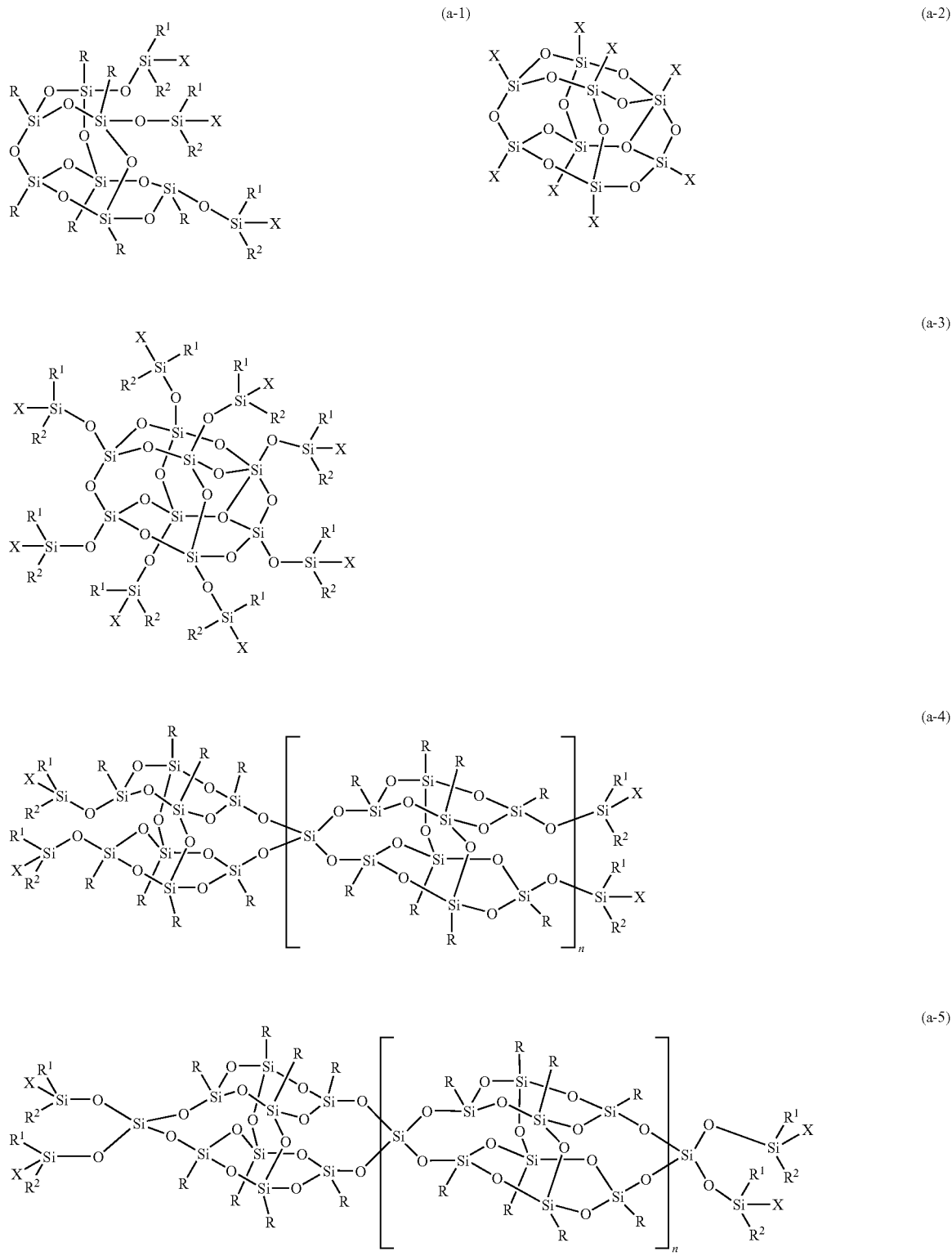

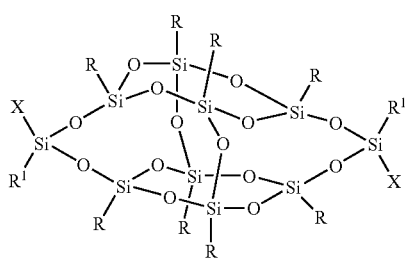

(a-6)

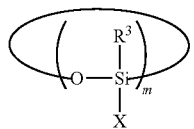

(a-7)

In the formulae (a-1), (a-4), (a-5) and (a-6), R represents a group selected independently from alkyl having 1 to 45 carbon atoms, cycloalkyl having 4 to 8 carbon atoms, aryl having 6 to 14 carbon atoms and arylalkyl having 7 to 24 carbon atoms. In the alkyl having 1 to 45 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced. In the benzene ring in the aryl and the arylalkyl, arbitrary hydrogen may be replaced by halogen or alkyl having 1 to 10 carbon atoms, and in the alkyl having 1 to 10 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced. The alkylene in the arylalkyl has 1 to 10 carbon atoms, in which in the alkylene, arbitrary —$CH_2$— may be replaced by —O—, provided that two —$CH_2$— adjacent to each other are not simultaneously replaced.

R preferably represents a group selected independently from cyclopentyl, cyclohexyl, phenyl and alkyl having 1 to 10 carbon atoms. In the alkyl having 1 to 10 carbon atoms, arbitrary hydrogen may be replaced by fluorine, and arbitrary —$CH_2$— may be replaced by —O—, provided that two —$CH_2$— adjacent to each other are not simultaneously replaced. In the phenyl, arbitrary hydrogen may be replaced by halogen, such as fluorine, or alkyl having 1 to 10 carbon atoms. R more preferably represents cyclopentyl, cyclohexyl, or phenyl, in which arbitrary hydrogen may be replaced by chlorine, fluorine, methyl, methoxy or trifluoromethyl, further preferably represents cyclohexyl of phenyl, and most preferably represents phenyl.

In the formulae (a-1), (a-3), (a-4), (a-5) and (a-6), $R^1$ and $R^2$ each represent a group selected independently from alkyl having 1 to 4 carbon atoms, cyclopentyl, cyclohexyl and phenyl. Examples of the alkyl having 1 to 4 carbon atoms include methyl, ethyl, propyl, 2-methylethyl, butyl and t-butyl. Preferred examples of $R^1$ and $R^2$ include methyl and phenyl. $R^1$ and $R^2$ preferably represent the same groups.

In the formula (a-7), $R^3$ represents a group selected independently from alkyl having 1 to 4 carbon atoms, cyclopentyl, cyclohexyl and phenyl. Examples of the alkyl having 1 to 4 carbon atoms include methyl, ethyl, propyl, 2-methylethyl, butyl and t-butyl. Preferred examples of $R^3$ include methyl and phenyl.

In the formulae (a-1) to (a-7), at least two occurrences per one molecule of X each represent hydrogen, and the remainder of X represents a group selected independently from alkyl having 1 to 4 carbon atoms, cyclopentyl, cyclohexyl and phenyl.

In the formulae (a-4) and (a-5), n represents an integer of 0 to 100.

In the formula (a-7), m represents an integer of 3 to 10.

More preferred example of the compound (A) include a compound represented by the following formula (a-4-1).

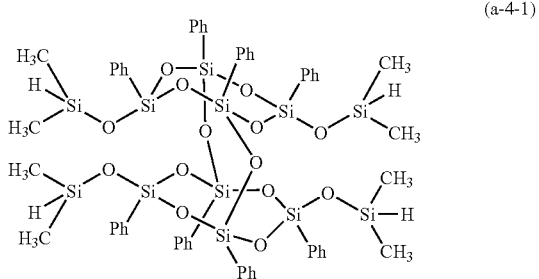

(a-4-1)

In the formula (a-4-1), Ph represents phenyl. The compound represented by the formula (a-4-1) can be synthesized according to the method disclosed in WO 2004/024741. The other compounds are available according to known methods.

Examples of the compound (B) include compounds represented by the following formulae (b-1) and (b-2).

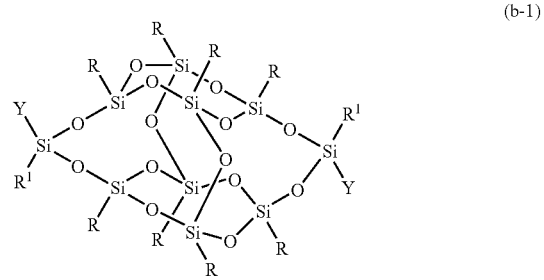

(b-1)

(b-2)

In the formula (b-1), R and $R^1$ each have the same meaning as R and $R^1$ for the formulae (a-1), (a-3), (a-4), (a-5) and (a-6), respectively, and preferred examples of R and $R^1$ are also the same.

In the formula (b-2), $R^4$ represents a group selected independently from alkyl having 1 to 4 carbon atoms, cyclopentyl, cyclohexyl and phenyl, and n represents an integer of 0 to 100.

In the formulae (b-1) and (b-2), Y represents a group selected independently from vinyl and allyl.

More preferred example of the compound (B) include compounds represented by the following formulae (b-1-1)

and (b-2-1). In the formula (b-2-1), $R^4$ represents a group selected independently from methyl and phenyl, and n represents an integer of 0 to 100.

(b-1-1)

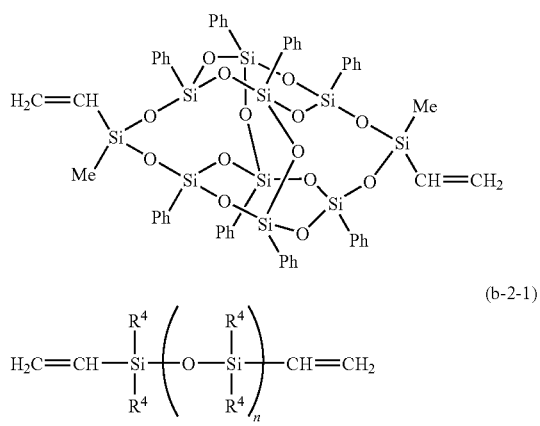

(b-2-1)

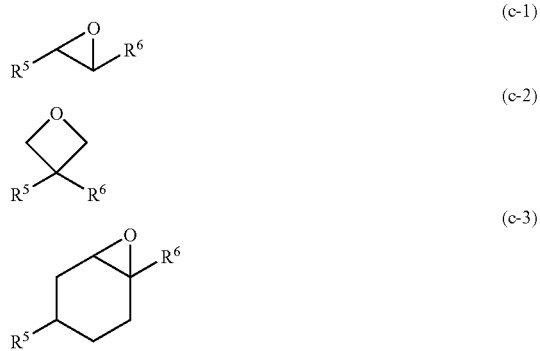

Specific examples of the compound represented by the formula (b-2-1) include 1,3-divinyl-1,1,3,3-tetramethyldisiloxane, 1,3-divinyl-1,3-dimethyl-1,3-diphenyldisiloxane and both-ends vinyl-terminated polydimethylsiloxane.

Examples of the compound (C) include compounds represented by the following formulae (c-1), (c-2) and (c-3).

(c-1)

(c-2)

(c-3)

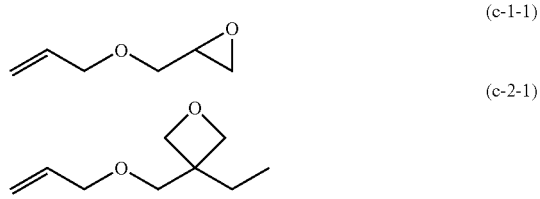

In the formulae (c-1), (c-2) and (c-3), one of $R^5$ and $R^6$ represents alkenyl having 2 to 10 carbon atoms, in which in the alkenyl, one —$CH_2$— may be replaced by —O— or 1,4-phenylene, and the other of $R^5$ and $R^6$ represents hydrogen or alkyl having 1 to 6 carbon atoms.

Preferred example of the compound (C) include compounds represented by the following formulae (c-1-1), (c-2-1), (c-3-1) and (c-3-2).

(c-1-1)

(c-2-1)

(c-3-1)

(c-3-2)

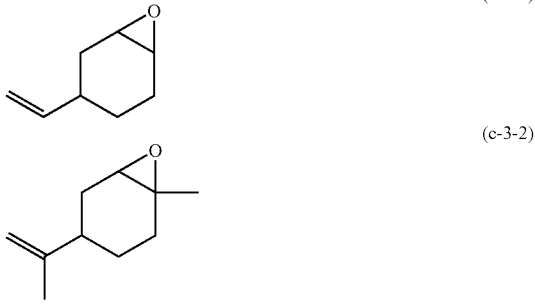

The compound represented by the formula (c-3-1) is commercially available from Daicel Chemical Industries, Ltd. under a trade name, Celloxide 2000.

Thermosetting Resin Composition

The thermosetting resin composition of the invention contains the organosilicon compound and a curing agent.

Examples of the curing agent include cyclohexane-1,3,4-tricarboxylic 3,4-anhydride (H-TMAn, available from Mitsubishi Gas Chemical Co., Ltd.) and other acid anhydrides.

Examples of the other acid anhydride include phthalic anhydride, maleic anhydride, trimellitic anhydride, pyromellitic anhydride, hexahydrophthalic anhydride, 3-methylcyclohexanedicarboxylic anhydride, 4-methylcyclohexanedicarboxylic anhydride, a mixture of 3-methylcyclohexanedicarboxylic anhydride and 4-methylcyclohexanedicarboxylic anhydride, tetrahydrophthalic anhydride, nadic anhydride, methylnadic anhydride, norbornane-2,3-dicarboxylic anhydride and methylnorbornane-2,3-dicarboxylic anhydride.

The ratio of the acid anhydride used in the thermosetting resin composition is preferably 3/7 to 7/3, and more preferably 4/6 to 6/4, in terms of a ratio of the molar number of the epoxy groups and the oxetanyl groups in the thermosetting resin and the molar number of the acid anhydride.

In the case where cyclohexane-1,3,4-tricarboxylic 3,4-anhydride is used as the curing agent, the molar ratio of cyclohexane-1,3,4-tricarboxylic 3,4-anhydride (which may be hereinafter referred to as H-TMAn) and the other acid anhydride may be 1/100 to 100/1, preferably 1/5 to 5/1, and particularly preferably 1/2 to 2/1. In the case where Rikacid (a trade name) MH-700G, available from New Japan Chemical Co., Ltd., is used as the other acid anhydride, it is preferably used by mixing at a ratio H-TMAn/MH-700G of 1/2.

The thermosetting resin composition of the invention may further contain a curing accelerator in addition to the curing agent.

Examples of the curing accelerator include a quaternary phosphonium salt, such as tetraphenylphosphonium bromide, tetrabutylphosphonium bromide, methyltriphenylphosphonium bromide, ethyltriphenylphosphonium bromide and n-butyltriphenylphosphonium bromide; a tertiary amine; a quaternary ammonium salt; a bicyclic amidine compound or a derivative thereof, such as 1,8-diazabicyclo[5.4.0]undecene-7; and an imidazole compound, such as 2-methylimidazole and 2-phenyl-4-methylimidazole, but the curing accelerator is not particularly limited as far as favorable curing property is obtained, and no coloration occurs. The curing accelerator may be used solely or as a combination of two or more kinds thereof. The bicyclic amidine compound, such as 1,8-diazabicyclo[5.4.0]undecene-7, and the imidazole compound are preferably used since they exhibit high activity with a small addition amount to the thermosetting resin composition, thereby curing the composition in a short period of time at a relatively low temperature, for example, in approximately 90 seconds at approximately 150° C. Preferred examples of the commercially available products thereof include Nikka Octhix Zinc (a trade name), available from Nihon Kagaku Sangyo Co., Ltd., and U-CAT 5003 (a trade name), available from San-Apro Ltd.

In the case where the curing accelerator is used, the ratio of the curing accelerator used is preferably 0.003 to 0.04, and more preferably 0.004 to 0.02, in terms of a weight ratio based on the total amount of the thermosetting resin composition. The use of the curing accelerator in an amount within the range provides sufficient curing acceleration effect without deterioration in property and coloration of the cured material.

The thermosetting resin composition of the invention may further contain a diluent.

Examples of the diluent include an organic solvent, an epoxy resin containing no silicon atom in the molecule thereof, and an oxetane resin containing no silicon atom in the molecule thereof. In the invention, a three-membered cyclic ether may be referred to as epoxy, a four-membered cyclic ether may be referred to as oxetanyl, a compound containing two or more epoxy groups per one molecule may be referred to as an epoxy resin and a compound containing two or more oxetanyl groups per one molecule may be referred to as an oxetane resin.

Examples of the organic solvent include a hydrocarbon solvent, such as hexane and heptane, an aromatic hydrocarbon solvent, such as benzene, toluene and xylene, an ether solvent, such as diethyl ether, tetrahydrofuran (THF) and dioxane, a halogenated hydrocarbon solvent, such as methylene chloride and carbon tetrachloride, an ester solvent, such as ethyl acetate, and a ketone solvent, such as acetone and 2-butanone. The solvents may be used solely or as a combination of two or more kinds thereof.

An epoxy resin containing no silicon atom in the molecule thereof and an oxetane resin containing no silicon atom in the molecule thereof are preferred as the diluent since they are cured along with the organosilicon compound of the invention by the curing agent. Specific examples of the epoxy resin containing no silicon atom in the molecule thereof include an epoxy resin, such as a bisphenol A type, a bisphenol F type, a bisphenol S type and a hydrogenated bisphenol A type, and an alicyclic epoxy resin, such as Celloxide 2021P, Celloxide 3000 and Celloxide 2081, trade names, available from Daicel Chemical Industries, Ltd. Specific examples of the oxetane resin containing no silicon atom in the molecule thereof include an oxetane resin, such as Aronoxetane, a trade name, available from Toagosei Co., Ltd. Examples of the diluent also include a silane coupling agent containing epoxy or oxetanyl in the molecule thereof. Specific examples of the silane coupling agent include SILA-ACE S510, S520 and S530, a trade name, available from Chisso Corporation.

The ratio of the oxetane resin containing no silicon atom in the molecule thereof, the epoxy resin containing no silicon atom in the molecule thereof and the silane coupling agent containing epoxy or oxetanyl in the molecule thereof is used, the ratio thereof added is generally 0 to 95% by weight, and preferably 0 to 75% by weight, based on the total amount of the thermosetting resin composition.

The thermosetting resin composition of the invention may contain an antioxidant. The addition of the antioxidant prevents deterioration due to oxidation under heat to provide a cured material suffering less coloration. Examples of the antioxidant include antioxidants of a phenol type, a sulfur type and a phosphorus type. The ratio of the antioxidant used is preferably 0.0001 to 0.1 in terms of a weight ratio based on the total amount of the thermosetting resin composition.

Specific examples of the antioxidant include a monophenol compound (such as 2,6-di-t-butyl-p-cresol, butylated hydroxyanisol, 2,6-di-t-butyl-p-ethylphenol and stearyl-β-(3,5-di-t-butyl-4-hydroxyphenyl)propionate), a bisphenol compound (such as 2,2'-methylenebis(4-methyl-6-t-butylphenol), 2,2'-methylenebis(4-ethyl-6-t-butylphenol), 4,4'-thiobis(3-methyl-6-t-butylphenol), 4,4'-butylidenebis(3-methyl-6-t-butylphenol) and 3,9-bis(1,1-dimethyl-2-(β-(3-t-butyl-4-hydroxy-5-methylphenyl)propionyloxy)ethyl)-2,4,8,10-tetraoxaspiro[5.5]undecane), a polymer type phenol compound (such as 1,1,3-tris(2-methyl-4-hydroxy-5-t-butylphenyl)butane, 1,3,5-trimethyl-2,4,6-tris(3,5-di-t-butyl-4-hydroxybenzyl)benzene, tetrakis(methylene-3-(3',5'-di-t-butyl-4'-hydroxyphenyl) propionate)methane, bis(3,3'-bis(4'-hydroxy-3'-t-butylphenyl)butyric acid) glycol ester, 1,3,5-tris (3',5'-di-t-butyl-4'-hydroxybenzyl)-S-triazine-2,4,6-(1H,3H,5H)trione and tocopherol), a sulfur antioxidant (such as dilauryl-3,3'-thiodipropionate, dimyristyl-3,3'-thiodipropionate and distearyl-3,3'-thiodipropionate), a phosphite compound (such as diphenyl phosphite, diphenyl isodecyl phosphite, phenyl diisodecyl phosphite, tris(nonylphenyl) phosphite, diisodecyl pentaerythritol phosphite, tris(2,4-di-t-butylphenyl)phosphite, cyclic neopentanetetraylbis (octadecyl)phosphite, cyclic neopentanetetraylbis(2,4-di-t-butylphenyl)phosphite, cyclic neopentanetetraylbis(2,4-di-t-butyl-4-methylphenyl)phosphite and bis(2-t-butyl-6-methyl-4-(2-(octadecyloxycarbonyl)ethyl)-phenyl) hydrogenphosphite), and an oxaphosphaphenanthrene oxide compound (such as 9,10-dihydro-9-oxa-10-phosphaphenanthrene-10-oxide, 10-(3,5-di-t-butyl-4-hydroxybenzyl)-9,10-dihydro-9-oxa-10-phosphaphenanthrene-10-oxide and 10-decyloxy-9,10-dihydro-9-oxa-10-phosphaphenanthrene-10-oxide). These antioxidants may be used solely, and in particular, a phenol antioxidant and a sulfur antioxidant, or a phenol antioxidant and a phosphorus antioxidant are preferably used in combination. Examples of the commercially available phenol antioxidant include Irganox 1010, a trade name, and Irgafos 168, a trade name, available from Ciba Specialty Chemicals Co., Ltd., which may be used solely or as a mixture thereof.

The thermosetting resin composition of the invention may contain an ultraviolet ray absorbent for enhancing the light resistance. Examples of the ultraviolet ray absorbent include an ordinary ultraviolet ray absorbent for plastics, and the ratio thereof is preferably 0.0001 to 0.1 in terms of a weight ratio based on the total amount of the thermosetting resin composition.

Specific examples of the ultraviolet ray absorbent include a salicylic acid compound, such as phenyl salicylate, p-t-butylphenyl salicylate and p-octylphenyl salicylate, a benzophenone compound, such as 2,4-dihydroxybenzophenone, 2-hydroxy-4-methoxybenzophenone, 2-hydroxy-4-octoxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methoxy-5-sulfobenzophenone, a benzotriazole compound, such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole and 2-((2'-hydroxy-3',3",4",5",6"-tetrahydrophthalimide-methyl)-5'-methyphenyl) benzotriazole, and a hindered amine compound, such as bis (2,2,6,6-tetramethyl-4-piperidyl) sebacate, bis(1,2,2,6,6- pentamethyl-4-piperidyl) sebacate and bis(1,2,2,6,6-pentamethyl-4-piperidyl)-((3,5-bis(1,1-dimethylethyl)-4-hydroxyphenyl)methyl)butyl malonate.

The thermosetting resin composition of the invention may further contain the following components (1) to (6).

(1) A reinforcing agent and a filler in the form of powder may be contained, examples of which include a metallic oxide, such as aluminum oxide and magnesium oxide, a silicon compound, such as fine powder silica, fused silica and crystalline silica, a transparent filler, such as glass beads, a metallic hydroxide, such as aluminum hydroxide, and other materials, such as kaolin, mica, quartz powder, graphite and molybdenum disulfide. These materials may be added in an amount within such a range that the thermosetting resin composition of the invention is not deteriorated in transparency. The mixing ratio thereof is preferably 0.10 to 1.0 in terms of a weight ratio based on the total amount of the thermosetting resin composition.

(2) A colorant and a pigment may be contained, examples of which include titanium dioxide, molybdenum red, iron blue, ultramarine blue, cadmium yellow, cadmium red and an organic colorant.

(3) A flame retardant may be contained, examples of which include antimony trioxide, a bromine compound and a phosphorus compound.

(4) An ion absorbent may be contained.

The mixing ratios of the components (2) to (4) each are preferably 0.0001 to 0.30 in terms of a weight ratio based on the total amount of the thermosetting resin composition.

(5) A silane coupling agent not containing epoxy and oxetanyl in the molecule may be contained.

(6) A dispersion of metallic oxide nanoparticles, such as zirconia, titania, alumina and silica, may be contained.

The mixing ratios of the components (1) to (6) each are preferably 0.01 to 0.50 in terms of a weight ratio based on the total amount of the thermosetting resin composition.

The cured material can be produced, for example, by the following manner. The organosilicon compound of the invention, cyclohexane-1,3,4-tricarboxylic 3,4-anhydride and the other acid anhydride are mixed, which are further mixed with the diluent depending on necessity. An antioxidant is added to the resulting mixture and mixed by stirring, followed by deaerated under reduced pressure. The mixture is cast in a mold and cured by heating to 125° C. for 1 hour, and finally to 150° C. for 2 to 3 hours.

The thermosetting resin composition of the invention may contain an additive, such as a curing accelerator, an antioxidant and an ultraviolet ray absorbent.

The transparency of the cured material can be evaluated by a yellowness index (YI) calculated according to JIS K7363 and the holding ratio of light transmittance, by measuring the transparency of the cured material before and after a heat resistance test using a ultraviolet visible spectrophotometer, which are preferably about 20 or less and 70% or more, respectively. The values within the ranges show that the cured material is colorless and has high transparency, and thus can be particularly preferably applied to such a purpose that requires transparency, such as a sealing material for an optical semiconductor device.

The cured material obtained by thermally curing the thermosetting resin composition of the invention may be molded to form a molded article, which may be applied to various purposes. Examples of the purposes include a sealing material for an optical semiconductor device, a sealing material for a semiconductor device, an insulating film, a sealing material, an adhesive and an optical lens.

EXAMPLES

The invention will be described in more detail with reference to examples. The invention is not limited to the examples.

The weight average molecular weight of silicone and silsesquioxane can be measured by the gel permeation chromatography (GPC) method. Specifically, silicone or silsesquioxane is diluted with tetrahydrofuran (THF) to a concentration of silicone or silsesquioxane of 0.05 to 0.10% by weight, and measured by the gel permeation chromatography (GPC) method by using a column KF-805L or KF-804L, available from Showa Denko Co., Ltd., with THF as a developer, thereby providing the weight average molecular weight of polymethyl methacrylate conversion.

Synthesis Example 1

The compound (1-1) was produced by the following scheme (1).

(1)

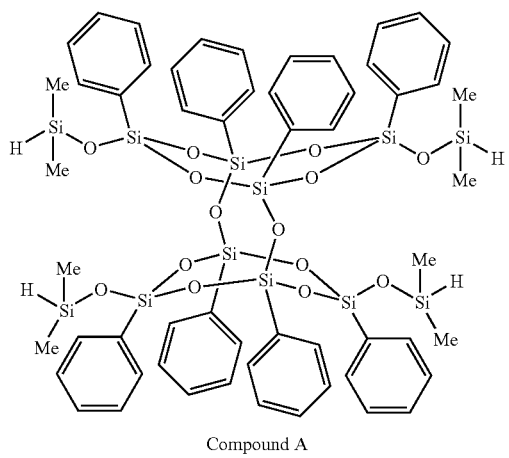

Compound A

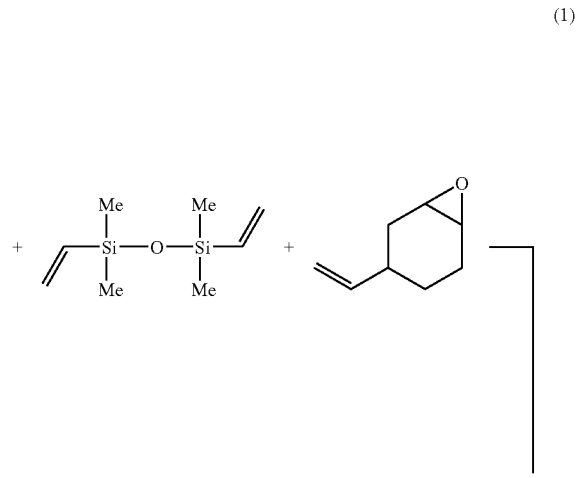

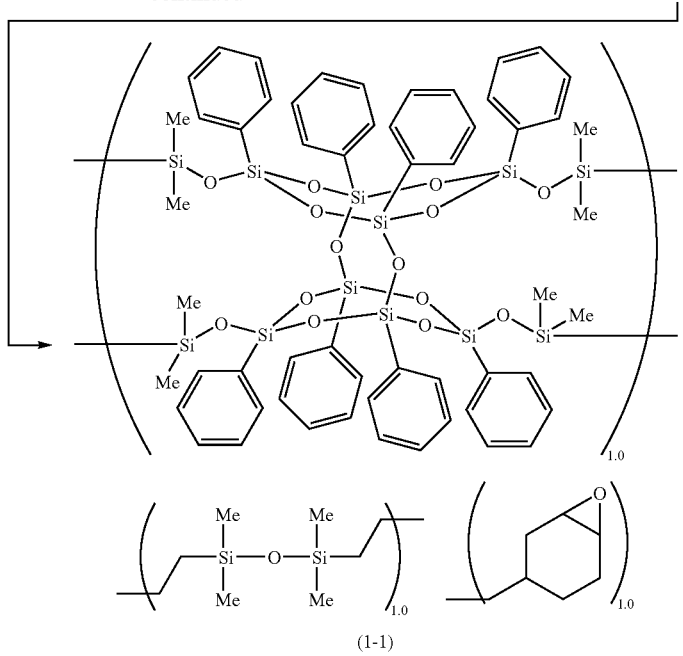

(1-1)

A compound (A) (80 g), which was synthesized by the method disclosed in WO 2004/024741 and dry toluene (80 g) were charged under a nitrogen atmosphere into a 500-mL reaction vessel equipped with a thermometer, a dropping funnel and a reflux condenser, and the reaction vessel was sealed with dry nitrogen. The mixture was heated to a reaction temperature of 80° C. under stirring with a magnetic stirrer. A Pt catalyst (16 µL) and 1,3-divinyl-1,1,3,3-tetramethyldisiloxane (available from Azmax Corporation) (11 g) were added thereto. The reaction mixture was heated to a refluxing temperature and stirred for 3 hours. The temperature was decreased to 80° C., and a Pt catalyst (16 µL) and Celloxide 2000 (product name: CEL2000), available from Daicel Chemical Industries, Ltd., (30.5 g) were added, followed by stirring for 2.5 hours. The reaction mixture was cooled to room temperature, and SH silica (available from Fuji Silysia Chemical Ltd.) (1.0 g) was added thereto, followed by stirring for 1 hour. The SH silica was removed by filtering, and the filtrate was concentrated with an evaporator. Acetone in an amount of 4 times the concentrate was added to the concentrate to prepare a 20% by weight solution. 3 g of activated carbon was added to the solution, which was stirred for 1 hour. The activated carbon was removed by filtering, and the filtrate was concentrated with an evaporator. 110 g of a concentrate (compound (1-1)) in a colorless glassy state was obtained. The GPC analysis of the concentrate revealed that the number average molecular weight Mn was 3,600 and the weight average molecular weight Mw was 8,000. The epoxy equivalent of the compound (1-1) measured according to JIS K7236 was 920 g/mol.

Synthesis Example 2

The compound (1-2) was produced by the following scheme (2).

(2)

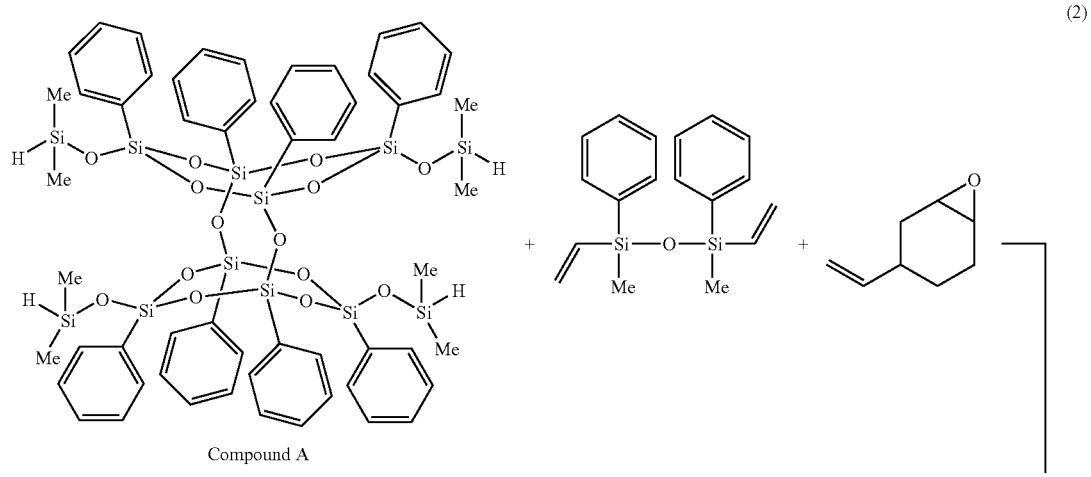

Compound A

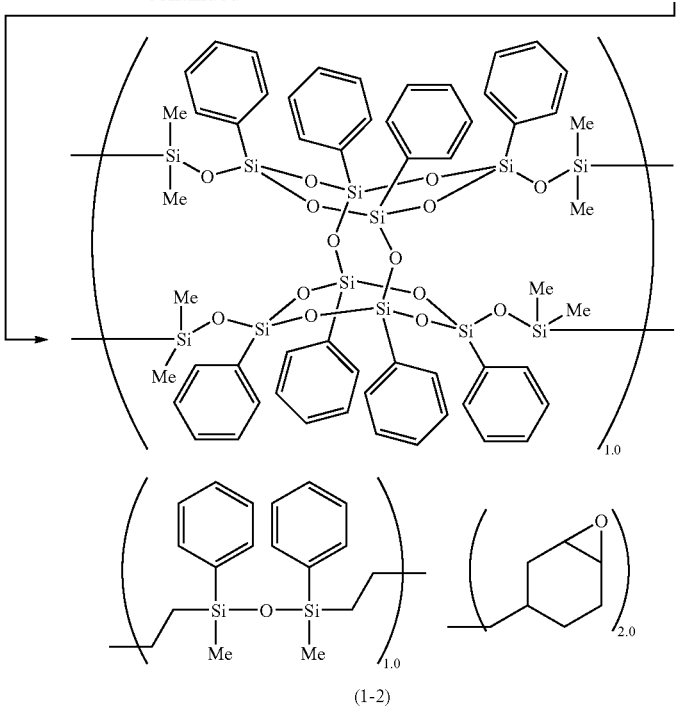

(1-2)

A compound (A) (32 g), which was synthesized by the method disclosed in WO 2004/024741 and dry toluene (32 g) were charged under a nitrogen atmosphere into a 500-mL reaction vessel equipped with a thermometer, a dropping funnel and a reflux condenser, and the reaction vessel was sealed with dry nitrogen. The mixture was heated to a reaction temperature of 80° C. under stirring with a magnetic stirrer. A Pt catalyst (16 μL) and 1,3-divinyl-1,3-dimethyl-1,3-diphenyldisiloxane (available from Azmax Corporation) (7.6 g) were added thereto. The reaction mixture was heated to a refluxing temperature and stirred for 3 hours. The temperature was decreased to 80° C., and a Pt catalyst (16 μL) was added, then Celloxide 2000 (product name: CEL2000), available from Daicel Chemical Industries, Ltd., (9.2 g) was added, followed by stirring for 2 hours. The reaction mixture was cooled to room temperature, and SH silica (available from Fuji Silysia Chemical Ltd.) (0.5 g) was added thereto, followed by stirring for 30 minutes. The SH silica was removed by filtering, and the filtrate was concentrated with an evaporator. Acetone in an amount of 4 times the concentrate was added to the concentrate to prepare a 20% by weight solution. 3 g of activated carbon was added to the solution, which was stirred overnight. The activated carbon was removed by filtering, and the filtrate was concentrated with an evaporator. 43 g of a concentrate (compound (1-2)) in a colorless glassy state was obtained. The GPC analysis of the concentrate revealed that the number average molecular weight Mn was 3,500 and the weight average molecular weight Mw was 7,000. The epoxy equivalent of the compound (1-2) measured according to JIS K7236 was 910 g/mol.

Synthesis Example 3

The compound (1-3) was produced by the following scheme (3).

(3)

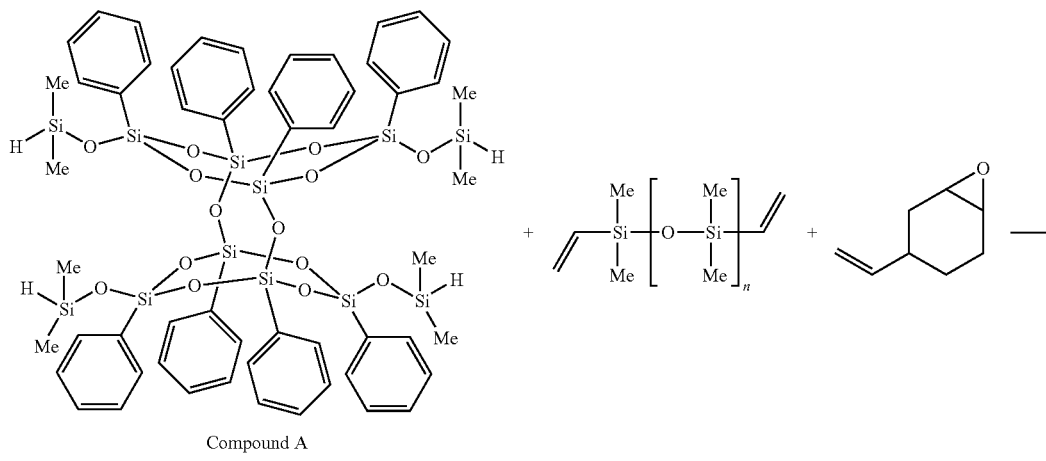

Compound A

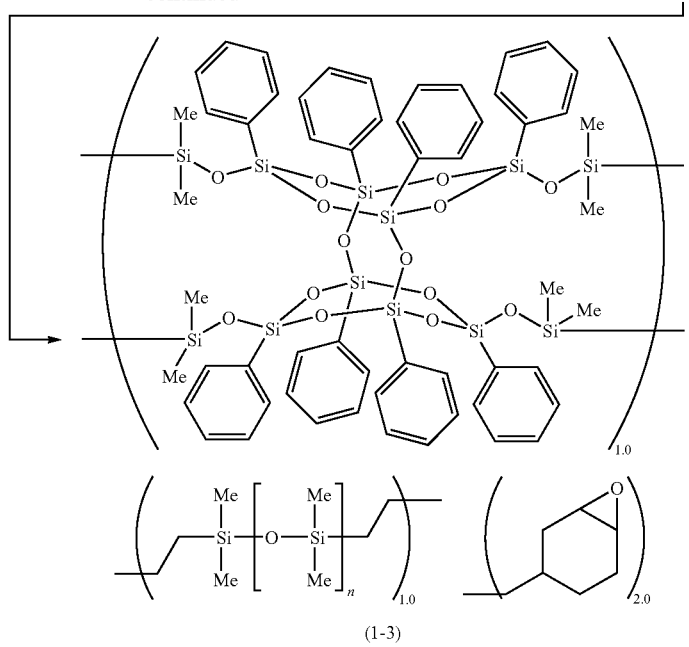

(1-3)

A compound (A) (16 g), which was synthesized by the method disclosed in WO 2004/024741 and dry toluene (16 g) were charged under a nitrogen atmosphere into a 500-mL reaction vessel equipped with a thermometer, a dropping funnel and a reflux condenser, and the reaction vessel was sealed with dry nitrogen. The mixture was heated to a reaction temperature of 80° C. under stirring with a magnetic stirrer. A Pt catalyst (16 μL) and both-ends vinyl-terminated polydimethylsiloxane DMS-V05 (available from Azmax Corporation, weight average molecular weight Mw: 2,500) (9.84 g) were added thereto. The reaction mixture was heated to a refluxing temperature and stirred for 3 hours. The temperature was decreased to 80° C., and Celloxide 2000 (product name: CEL2000), available from Daicel Chemical Industries, Ltd., (6.2 g) was added, followed by stirring for 2 hours. The reaction mixture was cooled to room temperature, and SH silica (available from Fuji Silysia Chemical Ltd.) (0.2 g) was added thereto, followed by stirring for 30 minutes. The SH silica was removed by filtering, and the filtrate was concentrated with an evaporator. Acetone in an amount of 4 times the concentrate was added to the concentrate to prepare a 20% by weight solution. 1 g of activated carbon was added to the solution, which was stirred overnight. The activated carbon was removed by filtering, and the filtrate was concentrated with an evaporator. 29.2 g of a concentrate (compound (1-3)) in a colorless glassy state was obtained. The GPC analysis of the concentrate revealed that the number average molecular weight Mn was 9,200 and the weight average molecular weight Mw was 79,000. The epoxy equivalent of the compound (1-3) measured according to JIS K7236 was 1,300 g/mol.

Comparative Synthesis Example 1

The compound (1-4) was produced by the following scheme (4).

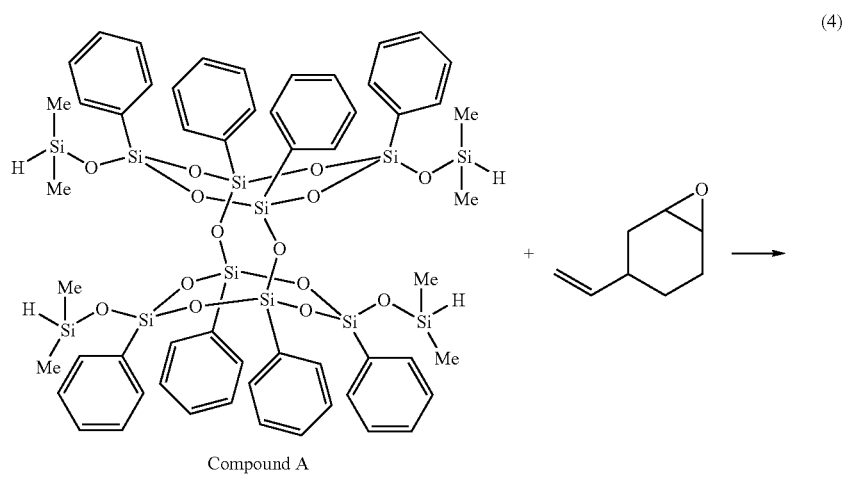

Compound A (4)

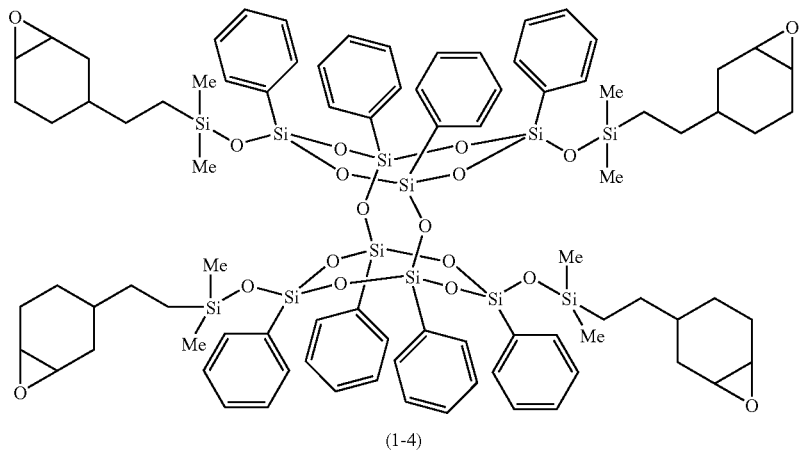

(1-4)

A compound (A) (21.0 g), which was synthesized by the method disclosed in WO 2004/024741 and dry toluene (20 g) were charged under a nitrogen atmosphere into a 200-mL reaction vessel equipped with a thermometer, a dropping funnel and a reflux condenser, and the reaction vessel was sealed with dry nitrogen. The mixture was heated to a reaction temperature of 60° C. under stirring with a magnetic stirrer. A Pt catalyst (21 μL) was added with a microsyringe, and Celloxide 2000 (product name: CEL2000), available from Daicel Chemical Industries, Ltd., (10 g) was slowly added dropwise through the dropping funnel, followed by stirring for 3 hours. The content of the reaction vessel was placed in an evaporator and concentrated to provide crude crystals. Acetone was added to the resulting crude crystals to prepare a 20% by weight solution. Activated carbon in an amount of 3% by weight based on the crude crystals was added to the solution, followed by stirring for 1 hour. Thereafter, the activated carbon was removed by filtering, and hexane in an amount 10 times the amount of the crude crystals was added to the solution, followed by stirring for 2 hours at 25° C. The solution was then filtered, and the filtrate was concentrated with an evaporator. Hexane in an amount of 1.25 times the amount of the resulting crude crystals was added thereto, and the crude crystals were dissolved therein by heating to 60° C. and then recrystallized at 25° C. The NMR analysis of the resulting crystals (yield amount: 22 g, yield: 76%) revealed that the crystals were the compound (1-4).

Major Materials Used in Examples

Silsesquioxane Derivative:
 Compounds (1-1), (1-2) and (1-4) produced in Synthesis Examples Curing Agent:
 Cyclohexane-1,3,4-tricarboxylic 3,4-anhydride (H-TMAn, available from Mitsubishi Gas Chemical Co., Ltd.)
 Hexahydrophthalic anhydride (MH-700G, available by New Japan Chemical Co., Ltd.)

Diluent:
 Epoxy resin (Celloxide CEL2021P, available from Daicel Chemical Industries, Ltd.)
 Silane coupling agent (S530, available from Chisso Corporation)

Additive:
 Antioxidant (Irganox 1010, available from Ciba Specialty Chemicals Co., Ltd.)
 Antioxidant (Irgafos 168, available from Ciba Specialty Chemicals Co., Ltd.)

Examples 1 to 4

Preparation of Cured Material

A mixture of the synthesized product (the compound (1-1) or (1-2)) in Synthesis Example 1 or 2 and a reactive diluent was placed in a screw tube, to which a mixture of H-TMAn, MH700G and the additive was then added. The screw tube was attached to a rotation-revolution mixer (Thinky Mixer ARE-250, available from Thinky Co., Ltd.), and the materials were mixed and defoamed to prepare a varnish. The varnish was poured into a petri dish made of Teflon (a trade name), available from Flon Industry Co., Ltd. The varnish poured into the petri dish was cured by placing in an oven heated to 125° C. The curing operation was carried out by heating to 125° C. for 1 hour and then 150° C. for 3 hours. The resulting cured material was cut with a band saw and polished with a Multiprep sample polisher (Item No. 15-2000, available from Allied High Tech Products, Inc.) to prepare a sample for measurement. The charged amounts of the components are shown in Table 1.

Comparative Example 1

Preparation of Cured Material

A cured product was produced in the same manner as in Examples 1 to 4 except that an epoxy resin (Celloxide CEL2021P, available from Daicel Chemical Industries, Ltd.) was used instead of the compound (1-1) or (1-2).

Comparative Example 2

Preparation of Cured Material

A cured product was produced in the same manner as in Examples 1 to 4 except that a mixture of the compound (1-4) and an epoxy resin (Celloxide CEL2021P, available from Daicel Chemical Industries, Ltd.) was used instead of the compound (1-1) or (1-2).

TABLE 1

Compositions of cured materials in Examples 1 to 4 and Comparative Examples 1 and 2

|  | Example 1 | Example 2 | Example 3 | Example 4 | Comparative Example 1 | Comparative Example 2 |
|---|---|---|---|---|---|---|
| Compound (1-1) (g) | 9.00 | 9.00 | — | — | — | — |
| Compound (1-2) (g) | — | — | 6.75 | 6.75 | — | — |
| Compound (1-4) (g) | — | — | — | — | — | 2.00 |
| S530 (g) | 3.00 | — | 2.25 | — | — | — |
| CEL2021P (g) | — | 3.00 | — | 2.25 | 6.00 | 6.00 |
| MH700G (g) | 2.43 | 3.72 | 1.81 | 3.71 | 5.28 | 5.77 |
| H-TMAn (g) | 0.80 | 1.23 | 0.60 | 1.22 | 1.74 | 1.90 |
| Irganox 1010 (mg) | 11.4 | 12.7 | 11.3 | 12.7 | 9.80 | 11.8 |
| Irgafos 168 (mg) | 34.3 | 38.1 | 22.6 | 38.1 | 29.3 | 35.3 |

Total Light Transmittance and Turbidity

The cured material was polished to flat on both surfaces thereof to a thickness of 3 mm to provide a test piece, which was measured for total light transmittance, diffuse transmittance and turbidity with a haze meter (NHD 5000, available from Nippon Denshoku Industries Co., Ltd.).

Refractive Index

The cured material was cut with a band saw, and a test piece was produced according to JIS K7142. The test piece was measured for refractive index with an Abbe refractometer (NAR-2T, available from Atago Co., Ltd.) using the D line (586 nm) of a sodium lamp. Methylene iodide was used as a contact liquid.

Shore Hardness

A test piece was produced from the cured material according to JIS B7727. The test piece was measured for hardness with a shore hardness tester (ASH-D, available from Mitutoyo Corporation).

Heat Resistance Test

The heat resistance was measured and evaluated in the following manner. Two test pieces of the cured material having a thickness of 3 mm after polishing and measured for light transmittance with an ultraviolet and visible spectrophotometer (V-660, produced by JASCO Corporation), and the transmittance at a wavelength of 400 nm was designated as an initial transmittance. The yellowness index (YI) calculated from the spectrum was designated as an initial yellowness index (YI). The test pieces were placed and processed in an oven (blower thermostat dryer, DRM420DA, available from Advantec Toyo Co., Ltd.) at 150° C. or 180° C. for 168 hours.

The cured materials after the processing were measured for spectrum with an ultraviolet and visible spectrophotometer (V-660, produced by JASCO Corporation), and from the transmittance at a wavelength of 400 nm, the holding ratio at 400 nm was calculated by the following expression. The yellowness index (YI) of the cured material was calculated and evaluated.

transmittance holding ratio (%)=((transmittance after processing for 168 hours)/(initial transmittance))×100

Adhesion Strength Test

A polyphthalamide resin (Amodel (a trade name) A-4122NLWH905, available from Solvay Advanced Polymers Co., Ltd.) was molded into a plate having a thickness of 2 mm to provide a substrate, and a test piece was produced by adjusting the dimension according to JIS K6850. The test piece was subjected to an adhesion test with a tensile and compressional tester (Strograph V10-C, produced by Toyo Seiki Seisaku-sho, Ltd.) using a 5 kN load cell.

The evaluation results of the test pieces obtained in Examples 1 to 4 and Comparative Examples 1 and 2 are shown in Table 2.

TABLE 2

|  |  | Example 1 | Example 2 | Example 3 | Example 4 | Comparative Example 1 | Comparative Example 2 |
|---|---|---|---|---|---|---|---|
| Total light transmittance (%) | | 92 | 92 | 92 | 92 | 92 | 92 |
| Turbidity | | 0.5 | 0.5 | 0.5 | 0.5 | 0.6 | 0.5 |
| Refractive index | | 1.52 | 1.53 | 1.53 | 1.53 | 1.51 | 1.51 |
| Shore Hardness | | 72 | 75 | 72 | 79 | 91 | 88 |
| Transmittance at 400 nm (%) | | 88 | 88 | 88 | 88 | 87 | 88 |
| Yellowness index | | 1.2 | 1.3 | 1.0 | 1.2 | 1.5 | 1.5 |
| Heat resistance test at 150° C. | Holding ratio of transmittance (%) | 94 | 90 | 94 | 87 | 77 | 83 |
| | Yellowness index | 2.3 | 4.9 | 2.8 | 5.2 | 8.8 | 7.8 |
| Heat resistance test at 180° C. | Holding ratio of transmittance (%) | 80 | 42 | 61 | 47 | 25 | 29 |
| | Yellowness index | 9.3 | 27.9 | 14.9 | 23.6 | 40.3 | 36.0 |
| Adhesion strength (MPa) | | — | — | 1.9 | 2.2 | 2.3 | 1.8 |

It is understood from the aforementioned results that the cured materials obtained by using the thermosetting resin compositions according to the invention are transparent, have a high refractive index, and are excellent in heat yellowing resistance, while maintaining large adhesion strength that was equivalent to a conventional epoxy resin. It is also understood that the cured materials are excellent in insulating property since they have a double-decker silsesquioxane structure.

Accordingly, the cured products are favorably applied to such purposes as an optical semiconductor device, a sealing material for a semiconductor device, an insulating film, a sealing material, an adhesive and an optical lens.

What is claimed is:

1. An organosilicon compound which is obtained by subjecting a compound (A), a compound (B) and a compound (C) to hydrosilylation reaction:
   (A) silicone and/or silsesquioxane that has two or more Si—H groups per one molecule and has a molecular weight of 100 to 500,000;
   (B) silicone and/or silsesquioxane that has two or more alkenyl groups per one molecule and has a molecular weight of 100 to 500,000, wherein at least one of the compound (A) and compound (B) is silsesquioxane; and
   (C) a compound that has one or more epoxy or oxetanyl group and an alkenyl group having 2 to 18 carbon atoms per one molecule.

2. The organosilicon compound according to claim 1, wherein
   the compound (A) is at least one compound selected from the group consisting of compounds represented by the formulae (a-1) to (a-7);
   the compound (B) is at least one compound selected from the group consisting of compounds represented by the formulae (b-1) and (b-2); and
   the compound (C) is at least one compound selected from the group consisting of compounds represented by the formulae (c-1), (c-2) and (c-3):

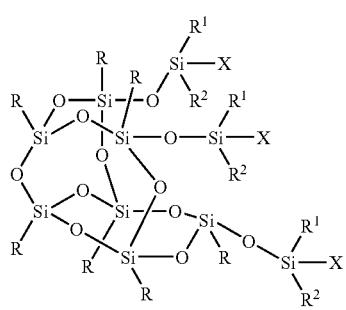

(a-1)

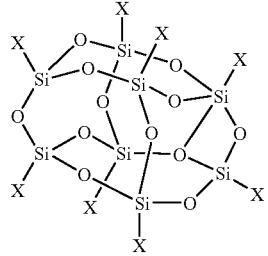

(a-2)

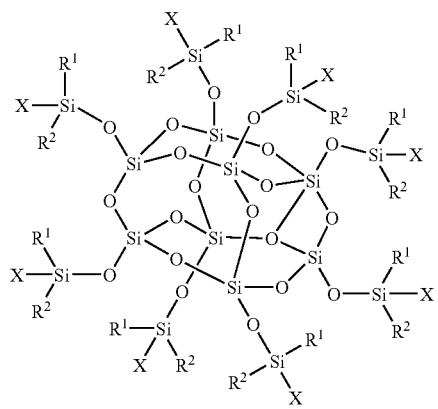

(a-3)

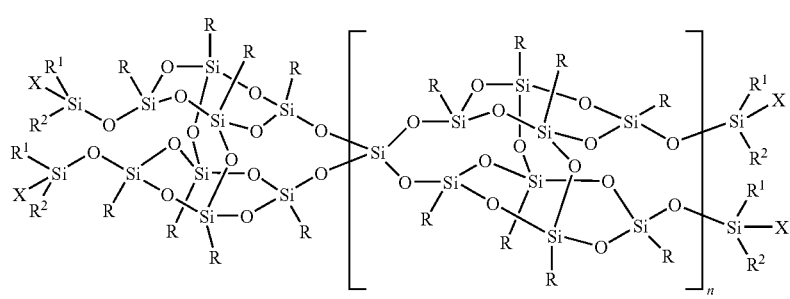

(a-4)

-continued

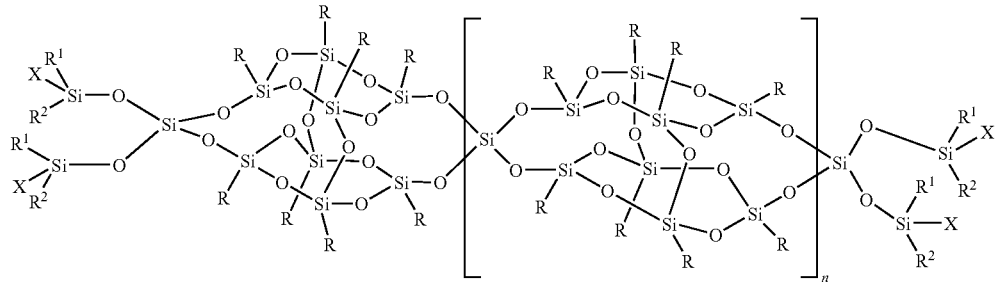
(a-5)

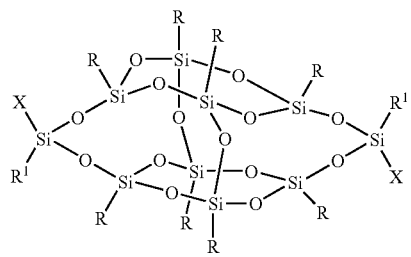
(a-6)

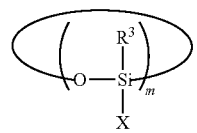
(a-7)

wherein
in the formulae (a-1) to (a-7),

R represents a group selected independently from alkyl having 1 to 45 carbon atoms, cycloalkyl having 4 to 8 carbon atoms, aryl having 6 to 14 carbon atoms and arylalkyl having 7 to 24 carbon atoms, wherein in the alkyl having 1 to 45 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced;

in the benzene ring in the aryl and the arylalkyl, arbitrary hydrogen may be replaced by halogen or alkyl having 1 to 10 carbon atoms, and in the alkyl having from 1 to 10 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced; and the alkylene in the arylalkyl has 1 to 10 carbon atoms, in which in the alkylene, arbitrary —$CH_2$— may be replaced by —O—, provided that two —$CH_2$— adjacent to each other are not simultaneously replaced, $R^1$ and $R^2$ each represent a group selected independently from alkyl having 1 to 4 carbon atoms, cyclopentyl, cyclohexyl and phenyl, $R^3$ represents a group selected independently from alkyl having 1 to 4 carbon atoms, cyclopentyl, cyclohexyl and phenyl, at least two of X represent hydrogen, and the remainder of X represents a group selected independently from alkyl having 1 to 4 carbon atoms, cyclopentyl, cyclohexyl and phenyl, n represents an integer of 0 to 100, and m represents an integer of 3 to 10,

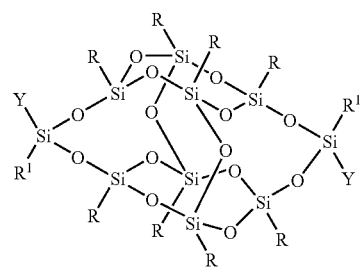
(b-1)

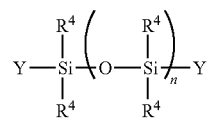
(b-2)

wherein
in the formulae (b-1) and (b-2),

R and $R^1$ each have the same meaning as R and $R^1$ for the formulae (a-1) to (a-6), respectively, $R^4$ represents a group selected independently from alkyl having 1 to 4 carbon atoms, cyclopentyl, cyclohexyl and phenyl, Y represents a group selected independently from vinyl and allyl, and n represents an integer of 0 to 100,

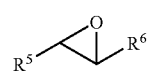
(c-1)

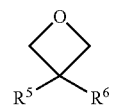
(c-2)

-continued

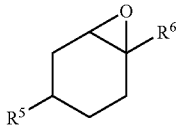
(c-3)

herein
in the formulae (c-1), (c-2) and (c-3),
one of $R^5$ and $R^6$ represents alkenyl having 2 to 10 carbon atoms in which one —$CH_2$— may be replaced by —O— or 1,4-phenylene, and the other of $R^5$ and $R^6$ represents hydrogen or alkyl having 1 to 6 carbon atoms.

3. The organosilicon compound according to claim 2, wherein the compound (B) is represented by the formula (b-1-1) or (b-2-1):

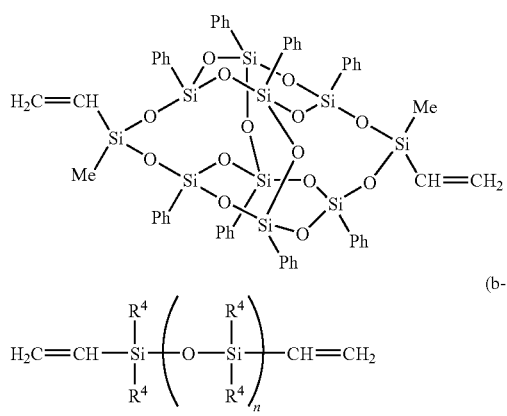

wherein $R^4$ represents a group selected independently from methyl and phenyl, and n represents an integer of 0 to 100.

4. The organosilicon compound according to claim 2, wherein the compound (C) is at least one compound selected from the group consisting of compounds represented by the formulae (c-1-1), (c-2-1), (c-3-1) and (c-3-2):

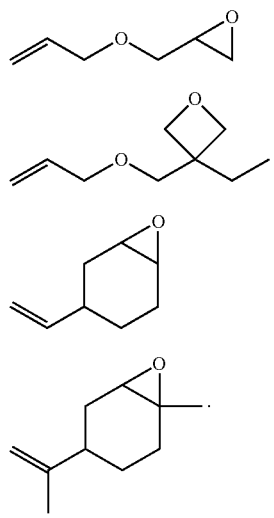

5. A thermosetting resin composition comprising the organosilicon compound according to claim 1, and a curing agent.

6. The thermosetting resin composition according to claim 5, wherein the curing agent is an acid anhydride.

7. The thermosetting resin composition according to claim 5, wherein the thermosetting resin composition further comprises a diluent, a curing accelerator and an additive.

8. The thermosetting resin composition according to claim 7, wherein the diluent is an epoxy resin containing no silicon atom in a molecule thereof, an oxetane resin containing no silicon atom in a molecule thereof, or an organic solvent.

9. The thermosetting resin composition according to claim 7, wherein the additive is an ultraviolet ray absorbent and/or an antioxidant.

10. A cured material which is obtained by heat-curing the thermosetting resin composition according to claim 5.

11. A molded article which is obtained by molding the cured material according to claim 10.

12. A coated film which is obtained by coating a film with the thermosetting resin composition according to claim 5.

13. An organosilicon compound which is obtained by subjecting a compound (A), a compound (B) and a compound (C) to hydrosilylation reaction:

(A) silicone and/or silsesquioxane that has two or more Si—H groups per one molecule and has a molecular weight of 100 to 500,000, wherein the compound (A) is a silsesquioxane derivative represented by the formula (a-4-1):

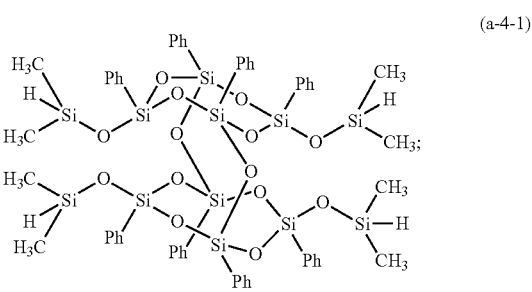
(a-4-1)

(B) silicone and/or silsesquioxane that has two or more alkenyl groups per one molecule and has a molecular weight of 100 to 500,000, wherein the compound (B) is at least one compound selected from the group consisting of compounds represented by the formulae (b-1) and (b-2); and (C) a compound that has one or more epoxy or oxetanyl group and an alkenyl group having 2 to 18 carbon atoms per one molecule, wherein the compound (C) is at least one compound selected from the group consisting of compounds represented by the formulae (c-1), (c-2) and (c-3):

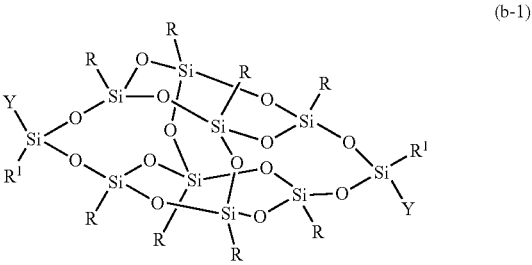
(b-1)

-continued

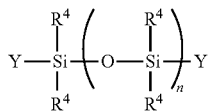
(b-2)

wherein
in the formulae (b-1) and (b-2),
R represents a group selected independently from alkyl having 1 to 45 carbon atoms, cycloalkyl having 4 to 8 carbon atoms, aryl having 6 to 14 carbon atoms and arylalkyl having 7 to 24 carbon atoms, wherein
in the alkyl having 1 to 45 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced;
in the benzene ring in the aryl and the arylalkyl, arbitrary hydrogen may be replaced by halogen or alkyl having 1 to 10 carbon atoms, and in the alkyl having from 1 to 10 carbon atoms, arbitrary hydrogen may be replaced by fluorine, and arbitrary —$CH_2$— may be replaced by —O— or —CH=CH—, provided that two —$CH_2$— adjacent to each other are not simultaneously replaced; and
the alkylene in the arylalkyl has 1 to 10 carbon atoms, in which in the alkylene, arbitrary —$CH_2$— may be replaced by —O—, provided that two —$CH_2$— adjacent to each other are not simultaneously replaced,
$R^1$ represents a group selected independently from alkyl having 1 to 4 carbon atoms, cyclopentyl, cyclohexyl and phenyl,
$R^4$ represents a group selected independently from alkyl having 1 to 4 carbon atoms, cyclopentyl, cyclohexyl and phenyl,
Y represents a group selected independently from vinyl and allyl, and
n represents an integer of 0 to 100, and

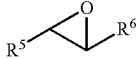
(c-1)

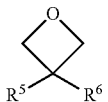
(c-2)

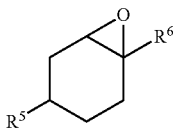
(c-3)

wherein
in the formulae (c-1), (c-2) and (c-3),
one of $R^5$ and $R^6$ represents alkenyl having 2 to 10 carbon atoms in which one —$CH_2$— may be replaced by —O— or 1,4-phenylene, and the other of $R^5$ and $R^6$ represents hydrogen or alkyl having 1 to 6 carbon atoms.

* * * * *